United States Patent
MacLeod et al.

(10) Patent No.: US 10,762,992 B2
(45) Date of Patent: Sep. 1, 2020

(54) SYNTHETIC GROUND TRUTH EXPANSION

(71) Applicant: Welltok, Inc., Denver, CO (US)

(72) Inventors: Matthew Kellar MacLeod, Denver, CO (US); Jacque W. Swartz, Loveland, CO (US); Marissa Victoria Ponder, Denver, CO (US)

(73) Assignee: Welltok, Inc., Denver, CO (US)

( * ) Notice: Subject to any disclaimer, the term of this patent is extended or adjusted under 35 U.S.C. 154(b) by 723 days.

(21) Appl. No.: 15/365,191

(22) Filed: Nov. 30, 2016

(65) Prior Publication Data

US 2018/0150607 A1    May 31, 2018

(51) Int. Cl.
*G16H 50/20*    (2018.01)
*G16H 10/20*    (2018.01)

(52) U.S. Cl.
CPC ............. *G16H 50/20* (2018.01); *G16H 10/20* (2018.01)

(58) Field of Classification Search
CPC ................................ G16H 50/20; G16H 10/20
USPC ............................................................. 706/46
See application file for complete search history.

(56) References Cited

U.S. PATENT DOCUMENTS

| | | | |
|---|---|---|---|
| 9,607,272 B1* | 3/2017 | Yu | G06N 20/00 |
| 2007/0185901 A1* | 8/2007 | Gates | G06F 16/355 |
| 2015/0161230 A1* | 6/2015 | Alkov | G06F 16/35 |
| | | | 707/737 |
| 2016/0180242 A1* | 6/2016 | Byron | G06N 20/00 |
| | | | 706/11 |
| 2016/0275414 A1* | 9/2016 | Towal | G06K 9/6256 |
| 2017/0032689 A1* | 2/2017 | Beason | G09B 7/00 |

OTHER PUBLICATIONS

Quan, Xiaojun. "Term Weighting Schemes for Question Categorization." IEEE Transactions on Pattern Analysis and Machine Intelligence, vol. 33, No. 5, May 2011, pp. 1009-1021. (Year: 2011).*

* cited by examiner

*Primary Examiner* — Shane D Woolwine
(74) *Attorney, Agent, or Firm* — Perkins Coie LLP

(57) ABSTRACT

A ground truth expansion system that generates an expanded set of synthetic questions and selects a targeted subset of questions for machine learning training. The machine learning may be used to train an automated inquiry system that responds to questions received from individuals about subject matter of interest. The automated inquiry system is particularly suitable for use in, for example, responding to questions raised by insured individuals about their healthcare benefits.

16 Claims, 7 Drawing Sheets

| Question Form | Intent | Synonyms | Answer Path |
|---|---|---|---|
| Can I get a <intent>? | Annual Physical | <physical exam, good-health visit, regular check-up, annual exam> | benefits_physical_exam_coverage |
| Am I covered for a <intent>? | Flu Vaccine | <flu, fever, influenza> <vaccine, shot, booster, immunization> | benefits_influenza_prevention_coverage |
| Does my insurance provide <intent>? | Counseling | <therapy, therapy sessions, outpatient counseling services> | benefits_mental_wellness_coverage |
| Hi. What can you tell me about <intent> coverage? | ... | ... | ... |
| ... | ... | | |

*FIG. 3*

SYNTHETIC GROUND TRUTH EXPANSION

BACKGROUND

As computing systems have increased in complexity, businesses have increasingly turned to artificial intelligence (AI) systems to provide services to employees and consumers. With proper training, AI systems can automate many of the tasks that were previously performed by teams of experts and perform these tasks at levels of sophistication, and with the benefit of insights, unattainable by humans. Key to the success of an AI system, however, is the ability of the system to find meaningfully complex patterns, which humans cannot identify, in a stream of input data. To identify patterns, an AI system is typically trained with a known dataset that exhibits the desired characteristics of the patterns to be detected. When building a dataset for training, the AI system designer must consider a number of incompatible design parameters. If the training dataset is too repetitive, the AI system can be too narrowly trained and may miss the detection of patterns that stray too far from those in the training dataset. If the training dataset is too small or focused, however, the AI system may do a poor job of detecting desired patterns and not reach a desired accuracy of detection. Constructing the right dataset for training can therefore involve a significant amount of trial-and-error by the AI system designer. Constructing training sets using trial-and-error is time consuming, costly, and ultimately frustrating to system designers. As such, a better method of generating training datasets of desired scope would therefore be beneficial to improving the functionality of AI systems.

BRIEF DESCRIPTION OF THE DRAWINGS

FIG. 3 is a table of sample question forms that are each mapped to answers responsive to the raised question.

DETAILED DESCRIPTION

Figure 1:
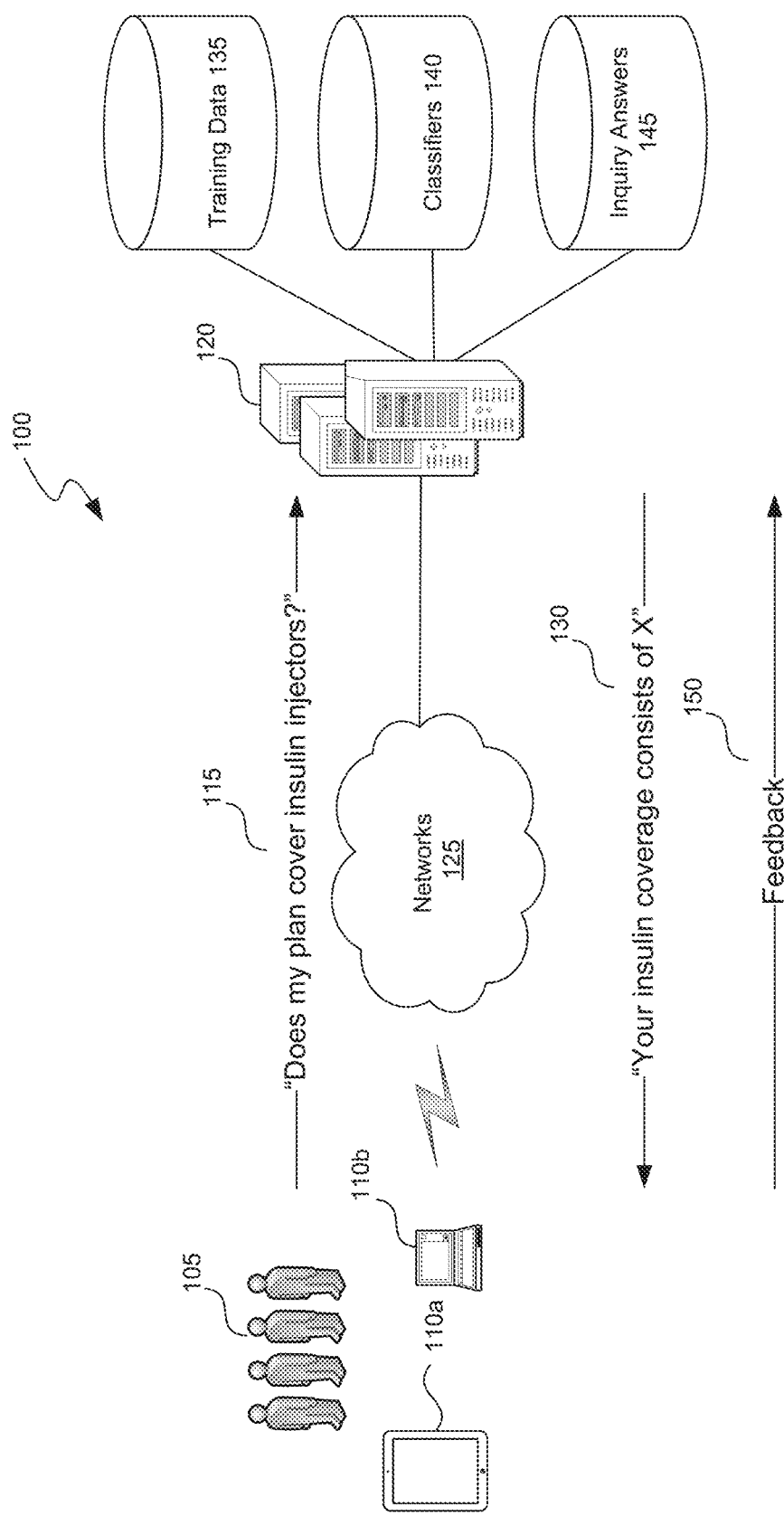
FIG. 1 is a diagram of a representative environment in which a synthetic ground truth expansion system ("GTX system") operates to generate training data for purposes of training a classifier in an automated inquiry system.

A ground truth expansion system that generates an expanded set of synthetic questions and selects a subset of questions for machine learning training is disclosed herein. The machine learning may be used to train an automated inquiry system that responds to questions received from individuals about subject matter of interest. The automated inquiry system is particularly suitable for use in, for example, responding to questions raised by insured individuals about their healthcare benefits.

The system maintains a training data template that includes different grammatical forms of questions that may be posed by an individual. The training data template also includes different intent phrases or intent utterances, each of which characterizes a topic on which the automated inquiry system is to be trained. For example, a first intent phrase may correspond to the topic of health insurance coverage for physical exams, a second intent phrase may correspond to the topic of health insurance coverage of flu shots, a third intent phrase may correspond to the topic of health insurance coverage for physical therapy, etc., where each is a topic on which the automated inquiry system may be queried (and thus needs to be trained). For each intent phrase the training data template additionally includes intent synonyms (i.e., alternative forms or phrases for referring to the intent phrase in a question), as well as answer information that addresses questions pertaining to the intent. For example, the training data template may include information for an intent referring to insurance coverage for an annual physical exam, a corresponding answer path to insurance coverage information for an individual, a set of synonyms based on terms that individuals may use to refer to insurance coverage and physical exams, and various question forms with which the question may be phrased.

Using the training data template, the system generates an expanded set of questions each associated with an answer. These question-and-answer pairs each represent known valid responses to the corresponding question, and a set of question-and-answer pairs forms a ground truth. Each ground truth may be built from question-and-answer pairs pertaining to a particular topic. For example, a ground truth may be generated that represents different ways in which annual physical exam insurance coverage questions can be asked and include the validated responses to the questions. The system facilitates the generation of different ground truths, each of which can be optimally formed for a different topic. As described herein, the system trains an automated inquiry system using the generated ground truths so that the system can effectively respond to other question forms from individuals regarding the trained topics.

To generate the synthetic ground truths, the system constructs questions based on combinations of question forms, intents, and synonyms from the training data template. For example, the training data template may include questions forms such as "am I covered for <intent>?," "does my insurance provide <intent>?," and "what can you tell me about <intent> coverage?," where <intent> indicates that different intent utterances or phrases, corresponding to different intents, may be used with the question form to construct a question for the intent. The training data template may further include, for an intent regarding insurance coverage for annual physical exams, synonyms such as "annual exam," "good-health visit," "regular check-up," "physical," and other terms or phrases commonly used by individuals to refer to their yearly physical exam. The system may accordingly, for example, generate a synthetic ground truth used for training an automated inquiry system to answer questions related to annual physical exam coverage with questions such as "am I covered for a good-health visit?," "does my insurance provide regular check-up coverage?," and "what can you tell me about physical exam coverage?." It will be appreciated that the system may utilize additional question forms and synonyms, as well as generate ground truths for different intents (e.g., coverage for a flu vaccine, coverage for physical therapy), thereby generating a large set of ground truth questions based on the template data for training the automated query system on different intents. In addition to generating questions based on synonym substitutions, the system also generates questions based on pronoun substitutions, thereby generating questions that refer to other parties having a relationship with the asking individual (i.e., a parent, spouse, child, other dependent, etc.) such as "is my wife covered for a good-health visit?." By doing so, the system constructs a large set of questions representing the various ways an individual may ask a question regarding an intent, both with respect to the individual as well as those having a relationship with the individual.

Though question construction is described primarily with respect to intent phrases (corresponding to topics) and corresponding synonyms, it will be appreciated that other forms of placeholders and substitutions may be used by the system. For example, question forms may include a <pronoun> placeholder for substitution of different pronouns. As a further example, question forms may include a <location> placeholder for substitution of different locations for obtaining care. That is, a question form of "Is <intent> available at <the location> for <pronoun>?" may be expanded to "Is care available at the urgent care facility for my daughter?," "Are diagnostic services available at the emergency room for my husband?," etc.

The set of synthetic questions, or candidate set, is analyzed by the system to determine a subset of questions to use for training an intent. The system selects from the candidate set a targeted subset of questions that achieves sufficient variety while reducing the number of questions used for training. By reducing repetition among the questions used, system performance is improved. Furthermore, obtaining enough variety with the targeted subset prevents overtraining the automated inquiry system on certain question types. That is, it avoids overfitting the automated inquiry system to particular forms of a question. The system is therefore able to synthetically generate ground truths used for training an intent that provide good training coverage without overly impacting system performance. It will be appreciated that the use of synthetic ground truths facilitates training an automated inquiry system to a sufficient level of confidence whereby individuals can reliably use the automated inquiry system. That is, synthetic ground truth generation reduces a significant obstacle to ground truth creation: the building of an initial ground truth to expose to users, who can then enrich the ground truth based on their interactions with the automated inquiry system. Such synthetic ground truth generation is particularly beneficial in the healthcare benefits space, where it is advantageous to roll-out automated benefits inquiry systems to individuals quickly due to the escalating costs of traditional benefits-answering system, and where the availability of conventional training data is often limited.

To select the targeted subset of questions for training an intent, the system characterizes each of the candidate questions associated with the intent as a vector. As described herein, the system uses the vector characterizations to compare the candidate questions and analyze their dissimilarity, thereby achieving question variety.

To generate the vector for a question, the system first deconstructs the plain question text into discrete text segments, such as n-grams and skip-grams. Each n-gram is a contiguous sequence of n items from the question text. For example, an n-gram of size 1 is referred to as a unigram, an n-gram of size 2 is referred to as a bigram, etc. The items can be for example, syllables, letters, or words. Accordingly, for example, a bigram of words is made up of two consecutive words from the question, and the question can be represented by a sequence of bigrams. As a further example, n-gram items may be composed of Parts of Speech, which facilitates the detection of question form patterns. For example, a Parts of Speech (PoS) bigram may be formed from ADJ-NOUN or ADJ-ADJ sequences. In addition to n-grams, the system may also deconstruct the plain question text into skip-grams, in which the skip-gram items (e.g., word or phrase pairs) are not necessarily consecutive in the question text being deconstructed. It will be appreciated that throughout the following, when describing system operation utilizing either n-grams or skip-grams, that either n-grams or skip-grams may be used. That is, for the sake of brevity, "n-grams" may be used throughout to refer to both n-grams and skip-grams. It will also be appreciated that n-grams or skip-grams of any size, and based on any constructs (e.g., phrases, words, PoS, phonemes, syllables, letters, etc.), and in any combination, may be used.

Each n-gram of the question being characterized is then analyzed to determine the importance of the n-gram to the question in the context of the expanded set of questions. For example, each n-gram may be characterized based on a numerical statistic, such as term frequency-inverse document frequency ("TF-IDF"), which is based on the frequency of the n-gram in the question being characterized as well as the infrequency of the n-gram in the expanded set of questions. That is, the TF-IDF value for an n-gram increases proportionally to the number of times the n-gram appears in a question, but is offset by the frequency of the n-gram in the expanded set of questions, thereby adjusting for the fact that certain n-grams appear more frequently in general. A vector is then generated for the question comprised of the TF-IDF values for each of the question n-grams.

The system selects the questions for training an intent based on comparisons of the vectors characterizing each of the questions, in the candidate set, associated with the intent. Various distance metrics, including cosine distance and other Euclidean distances, may be used to evaluate the distance between the TF-IDF vectors for different questions. The system then evaluates the vector distances between the candidate set questions associated with an intent to select the questions that, in combination, provide sufficient training variety. For example, the system may add questions to an initially empty training set by identifying questions that are sufficiently dissimilar (i.e., has a distance exceeding a threshold) from other questions in the training set. As a further example, the system may construct a training set that consists of all candidate questions, then remove questions from the training set that are too similar (i.e., has a distance within a threshold) to other questions in the training set. Questions may be added to or removed from the training set until a target number of questions in the training set is selected that achieves a target dissimilarity measure. Dissimilarity of the training set may be evaluated, for example, based on the average pairwise distances between vectors in the training set as well as an overall average distance for the set. The system then trains the automated inquiry system using the training set of questions. For example, the automated inquiry system may include different natural language classifiers associated with different intents (e.g., a classifier to recognize questions about flu shot coverage, a classifier to recognize questions about physical therapy coverage, etc.), and each classifier may be trained using the training set generated for the associated intent.

Various implementations of the system will now be described. The following description provides specific details for a thorough understanding and an enabling description of these implementations. One skilled in the art will understand, however, that the system may be practiced without many of these details. Additionally, some well-known structures and functions may not be shown or described in detail so as to avoid unnecessarily obscuring the relevant description of the various implementations. The terminology used in the description presented below is intended to be interpreted in its broadest reasonable manner, even though it is being used in conjunction with a detailed description of certain specific implementations of the system.

FIG. 1 and the following discussion provide a brief, general description of a suitable environment in which a synthetic ground truth expansion system ("GTX system") may be implemented. Although not required, aspects of the system are described in the general context of computer-executable instructions, such as routines executed by a general-purpose computer, a personal computer, a server, or other computing system. The system can also be embodied in a special purpose computer or data processor that is specifically programmed, configured, or constructed to perform one or more of the computer-executable instructions explained in detail herein. Indeed, the term "computer" and "computing device," as used generally herein, refer to devices that have a processor and non-transitory memory, like any of the above devices, as well as any data processor or any device capable of communicating with a network. Data processors include programmable general-purpose or special-purpose microprocessors, programmable controllers, application-specific integrated circuits (ASICs), programming logic devices (PLDs), or the like, or a combination of such devices. Computer-executable instructions may be stored in memory, such as random access memory (RAM), read-only memory (ROM), flash memory, or the like, or a combination of such components. Computer-executable instructions may also be stored in one or more storage devices, such as magnetic or optical-based disks, flash memory devices, or any other type of non-volatile storage medium or non-transitory medium for data. Computer-executable instructions may include one or more program modules, which include routines, programs, objects, components, data structures, and so on that perform particular tasks or implement particular abstract data types.

Aspects of the system can also be practiced in distributed computing environments, where tasks or modules are performed by remote processing devices, which are linked through a communications network, such as a Local Area Network ("LAN"), Wide Area Network ("WAN"), or the Internet. In a distributed computing environment, program modules or subroutines may be located in both local and remote memory storage devices. Aspects of the system described herein may be stored or distributed on tangible, non-transitory computer-readable media, including magnetic and optically readable and removable computer discs, stored in firmware in chips (e.g., EEPROM chips). Alternatively, aspects of the system may be distributed electronically over the Internet or over other networks (including wireless networks). Those skilled in the relevant art will recognize that portions of the system may reside on a server computer, while corresponding portions reside on a client computer.

FIG. 1 illustrates an example environment 100 in which a synthetic ground truth expansion system ("GTX system") operates. The environment may include one or more client computing devices 110 and server computers 120. The client computing devices 110 communicate with each other and the server computers 120 through networks 125 including, for example, the Internet. The client computing devices 110 may communicate wirelessly with a base station or access point using a wireless mobile telephone standard, such as the Global System for Mobile Communication (GSM), or another wireless standard, such as 802.11 or Bluetooth, and the base station or access point communicates with server computers 120 via the network 125.

Aspects of the GTX system may be practiced by the client computing devices 110 and the server computers 120. For example, individuals 105 using client computing devices 110 can ask questions 115 to an automated inquiry service running on server computers 120. The automated inquiry service may be part of a healthcare benefits service, and the individuals 105 may be insured individuals asking questions 115 about their healthcare benefits. For example, an individual 105 may ask the service whether their healthcare benefit plans covers insulin injectors. Based on maintained text classifiers and answers, described below, the server computers 120 respond to the question 115 with a response 130. As described herein, the text classifiers are trained using training data generated by the GTX system.

Answers to anticipated questions are maintained in inquiry answer storage area 145. For example, the inquiry answer storage area 145 may maintain information for answering questions related to healthcare benefits associated with treating insulin, associated with treating heart disease, or other questions that insured individuals 105 may have regarding their healthcare benefits. Different answers maintained in the inquiry answer storage area 145 may be associated with different topics corresponding to the type of questions for which the answer is an appropriate response. That is, one answer may be associated with the insulin injector coverage topic, and another answer associated with outpatient mental health services topic.

The automated inquiry service utilizes classifiers maintained in classifier storage area 140 to identify the topic of a received question 115. Each classifier may be associated with a particular topic and be capable of recognizing, based on natural language processing of the received question 115, whether the question pertains to the associated topic. It will be appreciated that the classifiers may be trained using supervised machine learning techniques based on a training data set of known correct outputs. For example, the training data set may include different questions and known topics and/or valid answers associated with each question. The training data may be maintained in training data storage area 135. As described herein, the GTX system generates sets of synthetic known-good questions and answers (or "ground truths") that are used to train the text classifiers.

To respond to the question 115, the server computers 120 analyze the question text using the text classifiers and identify the topic to which the question is directed. Based on the identified topic, the server computers 120 determine the appropriate response from the maintained automated inquiry answers. The response should address the individual's question, such as a response that includes relevant coverage information and may include other complementary information that might be beneficial to the individual. In the depicted example related to the question about insulin injectors, for example, the response 130 may provide details about the individual's insulin coverage but may also provide other coverage information related to, for example, diabetes treatment. The provided response 130 may, for example, be displayed on the client computing device 110 used by the individual 105 or converted to an auditory message that is played to the individual 105.

On a periodic or ongoing basis, the GTX system may retrain the text classifiers based on observed use by individuals 105 of the automated inquiry service. For example, the server computers 120 may receive feedback 150 regarding the accuracy of responses 130 provided to individuals 105. For example, the individual may provide explicit feedback using an interface element displayed on the client computing device 110 (e.g., a button to indicate that the response answered the question and a button to indicate that the response did not answer the question). As a further example, the system may determine the feedback 150 implicitly from the individual's next actions. For example, an individual 105 terminating the session with the answer inquiry service or responding with a "thank you" message may indicate that the response 130 addressed the individual's question, while asking a rephrased form of the question 115 may indicate that the response 130 failed to address the individual's original question. The server computers 120 use the feedback 150 to retrain the classifiers.

As a further example of use-based retraining, the system may analyze actual questions 115 posed by individuals 105. From those questions, the system may identify new question forms, intent synonyms, locations, and pronouns embedded in the observed questions. Using the techniques described herein, the system may construct new questions from the identified question forms and other question components. The system may then determine the measure of dissimilarity between the newly-constructed questions and the existing questions found in the training data for a text classifier, and if the new questions are adequately dissimilar, add them to the training data storage area 135. The text classifiers may then be retrained based on the expanded training set.

Training a Classifier Using a Synthetic Ground Truth

Figure 2:
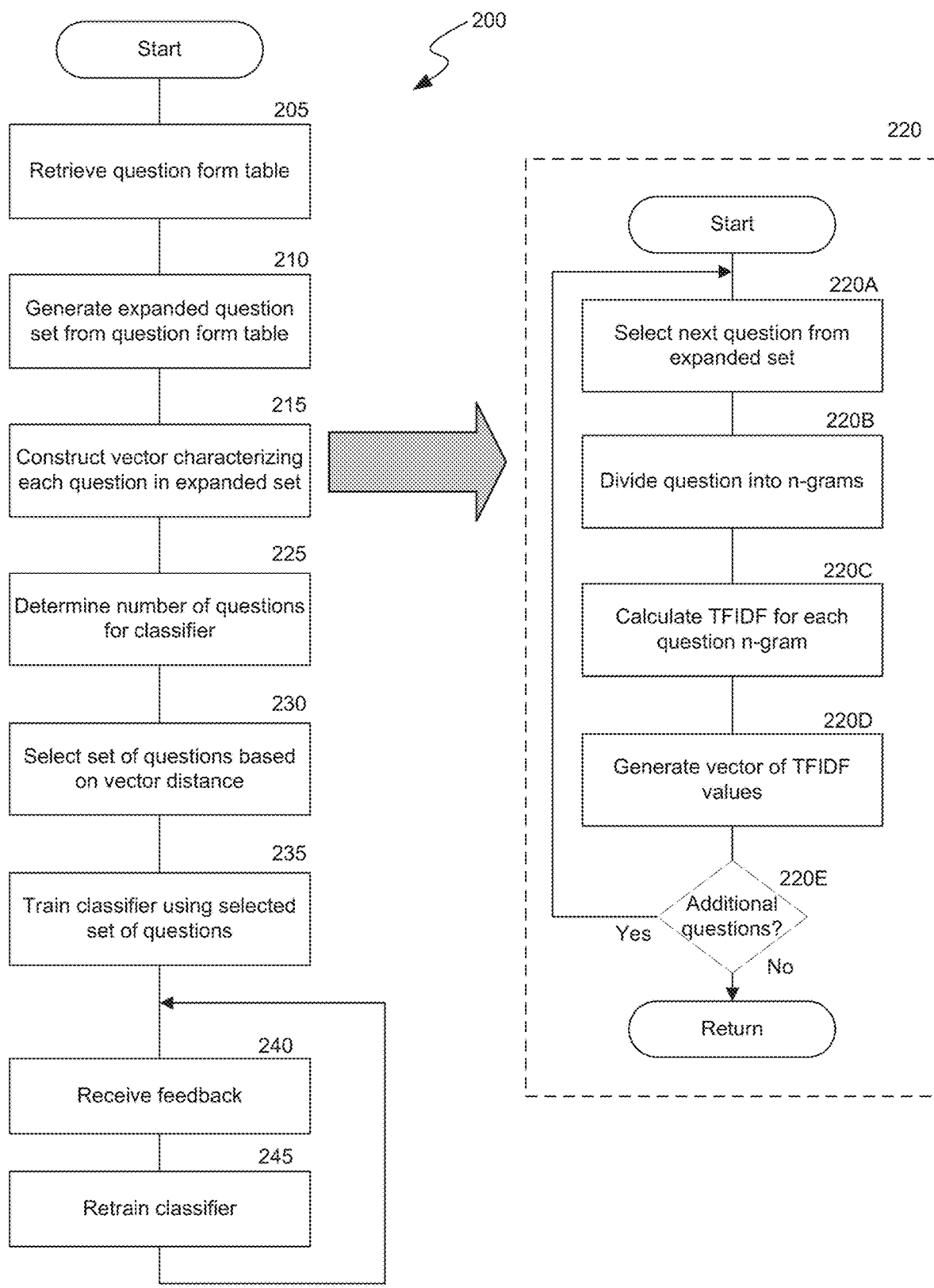
FIG. 2 is a flow chart of a method performed by the GTX system to generate a reduced set of diverse questions for purposes of training the classifier.

FIG. 2 is a flow diagram illustrating an example process 200, implemented by a ground truth expansion system, for generating a set of diverse questions to be used to train a text classifier. At a block 205, the system retrieves a question form table that describes the form and content of different question types. An example question form table is illustrated in FIG. 3.

FIG. 3 illustrates a table of question forms and answers 300, based on which synthetic ground truths are generated by the system. The table 300 includes a question form field 305, an intent field 310, a synonym field 315, and an answer path field 320. The question form field 305 describes different grammatical forms with which a question may be posted. For example, the table 300 includes as question forms "can I get an <intent>?" and "am I covered for a <intent>?." As described herein, an intent refers to the topic or content to which a specific question is directed, and as recited in the question form field 305 represents a placeholder marker in the question form. That is, generated questions will include an actual intent keyword or phrase in place of the "<intent>" marker. The question forms may also represent conversational styles consistent with an individual responding to a prompt from an automated inquiry system. For example, the table 300 includes the question form "Hi. What can you tell me about <intent> coverage?." As a further example, a question form could be "Hi. Thanks for asking. I have a question about <intent>." The table 300 is typically compiled by a system operator or other individual that is versed in the types of questions that are received for the associated topic. As described herein, the system generates questions for an intent based on multiple question forms.

The intent field 310 describes the topics to which different questions may be directed. For example, the table 300 includes intents "annual physical," "flu vaccine", and "counseling," corresponding to questions that could be asked regarding each of those topics. Although the illustrated intents are at a particular level of generality (e.g., "counseling"), the table 300 can include more or less specific intents (e.g., "out-of-network counseling costs" and "number of out-patient counseling services covered annually"). Each intent in the table 300 is associated with intent synonyms and an answer path, as provided by synonyms field 315 and answer path field 320, respectively. The synonyms field 315 provides the different keywords or phrases that may be used by an individual in a question but that the system treats as referring to the same intent. For example, as illustrated in table 300 the counseling intent may be indicated by the occurrence of the word "counseling" in a question, as well as by the occurrence of the synonyms "therapy," "therapy sessions," and "outpatient counseling services" in a question. The answer path field 320 provides information on the answer provided, by an automated inquiry service, to a question directed to the associated intent. The answer path field 320 may maintain, for example, the actual response text or, as illustrated in table 300, a path (e.g., a filename, a link, etc.) to a data source containing the response information. For example, as illustrated in table 300, questions with the annual physical intent are responded to with an answer from the benefits_physical_exam_coverage data source, while questions with the flu vaccine intent are responded to with an answer from the benefits_influenze_prevention_coverage data source. Answers may be stored as text, images, audio clips, video clips, interactive media, or any combination thereof.

Although the examples illustrated in the table 300 are representative of questions and answers pertaining to insurance coverage in a health benefits system, it will be appreciated that the table may be used for other contexts. Furthermore, though illustrated as a table in which fields are represented by columns and each row contains an entry, it will be appreciated that other data structures may be used.

Figure 4:
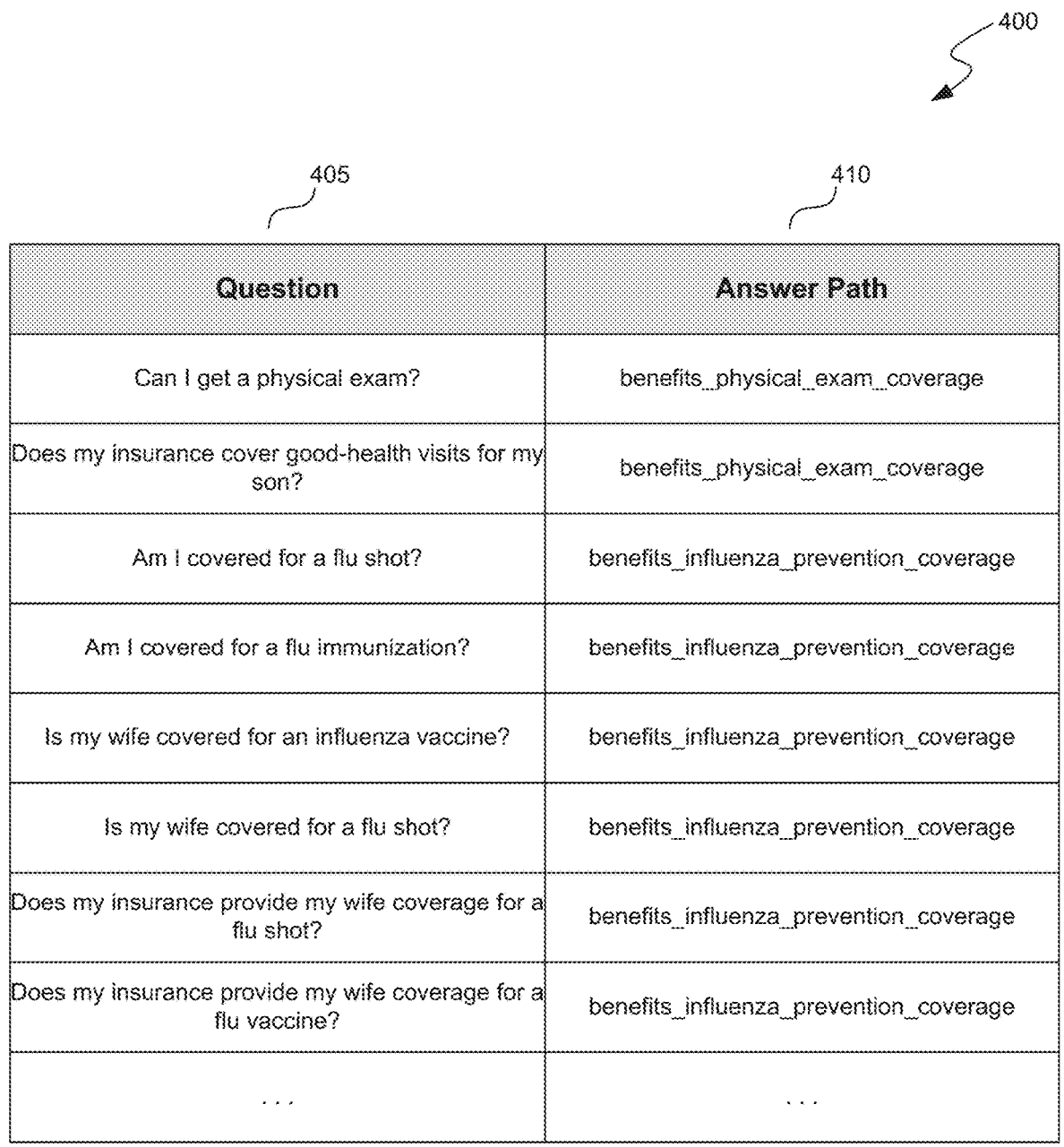
FIG. 4 is a table of an expanded candidate question set.

Returning to FIG. 2, at a block 210 the system generates an expanded question set from the question form table. Questions are generated by combining the question forms with listed intents and their associated synonyms. For example, referring again to the question form table 300 in FIG. 3, questions can be generating by substituting the phrase "annual physical" into each of the listed question forms. The question generation can then be repeated for each of the "annual physical" synonyms. All of the generated questions associated with "annual physical" and its synonyms may then be associated with the answer benefits_physical_exam_coverage. The questions generated for "annual physical" may also include questions generated based on pronoun or location substitution, in which the generated question refers to a person other than the asking individual (e.g., "my husband," "my wife," "my dependent," etc.) or to different locations where care is available. Questions may additionally be generated that substitute anaphoric or cataphoric references (e.g., "it," "one," "that," etc.) in place of prior or subsequent instances of a term, respectively. Question generation may further repeat for all of the intents recited in the question form table (e.g., "flu vaccine," "counseling," and others). That is, the expanded set of questions may include questions referring to different intent topics. FIG. 4 illustrates a table of expanded questions 400, which includes a question field 405 and answer path field 410, generated by the question set expansion of block 210.

Figure 5:
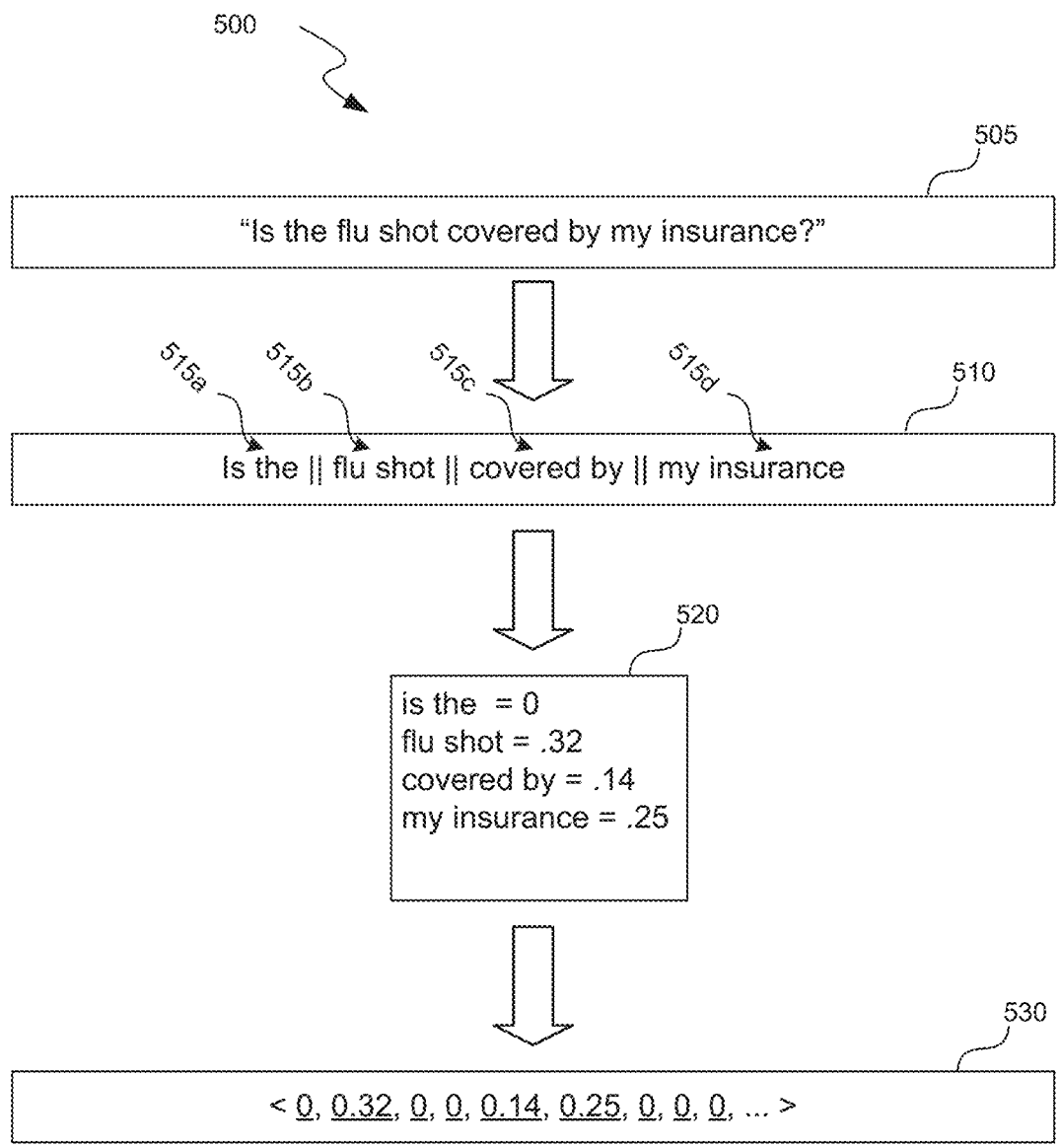
FIG. 5 is a diagrammatic representation of the construction of a vector characterizing a generated question.

At a block 215, the system constructs vectors characterizing each of the questions in the expanded set. Vector construction is illustrated in greater detail in sub-process 220, which comprises blocks 220A-220E, as well as FIG. 5, which illustrates a diagrammatic representation of vector construction.

At a block 220A, the system selects the next question from the generated set of questions. At a block 220B, the system divides the selected question into discrete units, or text segments, such as n-grams or skip-grams. As described, the system may divide the question into n-grams or skip-grams of different size (e.g., 1, 2, 3, etc.) and different constructs (e.g., words, syllables, letters, etc.). For example, referring to FIG. 5 and the representation of vector construction 500, a question "is the flu shot covered by my insurance?" 505 may be divided 510 into bigrams "is the," "flu shot," "covered by," and "my insurance" 515. Although the following description refers to n-grams, it will be understood that system may also utilize skip-grams throughout.

At a block 220C, the system calculates the term frequency-inverse document frequency (TF-IDF) of each n-gram of the selected question. The TF-IDF for an n-gram increases proportionally with the number of times the n-gram appears in the question, but is offset by the frequency of the n-gram in the generated set of questions. For example, the TF-IDF for an n-gram in a question may be calculated as:

$$TFIDF = f_{n,q} \times \ln \frac{N}{1 + c_q},$$

where $f_{n,q}$ represents the relative frequency of the n-gram in the question (based on the total count of the occurrences of the n-gram in the question and the total number of n-grams in the question), $c_q$ represents the number of generated questions that include the n-gram, and N represents the total number of generated questions. It will be appreciated that the TF-IDF for an n-gram may be calculated using other schemes that differently weight the term frequency and inverse document frequency components, and that statistical metrics other than TF-IDF may be used for characterizing the importance of a term in a question. Referring again to FIG. 5, example TF-IDF values 520 are illustrated for bigrams 515. For example, the bigram "is the" has a TF-IDF value of 0, indicating that the bigram is very common within the generated set of questions. In contrast, the bigram "flu shot" has a TF-IDF of 0.32, indicating that the bigram is relatively rare within the generated set of questions.

At a block 220D, the system constructs a vector representation of the question based on the calculated n-gram TF-IDF values. In some embodiments the vector is sized to have a number of elements corresponding to the number of n-grams in the set of generated questions, where each vector element position is associated with a unique n-gram. The ordering of n-gram positions in the vector may be based on, for example, the frequency of the n-gram in the set of generated questions, alphabetically, or other. The vector for a question may be constructed such that a vector element contains a '0,' or other indication, if the associated n-gram is not in the question text, and contains the calculated TF-IDF value if the n-gram is contained in the question text. It will be appreciated that other vector formats may be used. Referring again to FIG. 5, vector 530 illustrates a vector construction of question 505 based on calculated TF-IDF values 520.

At a decision block 220E, the system determines whether there are additional questions in the generated set for which vectors are to be constructed. If it is determined that there are additional questions, processing returns to block 220A for the selection of the next question in the set. If it is determined that there are no additional questions, the construction of vectors terminates and returns to the process 200.

Returning to the process 200, at a block 225 the system determines the number of questions that should be used to train the particular text classifier to be trained. For example, if a text classifier is associated with a narrowly focused intent (e.g., a question about the out-of-pocked costs for a specific procedure when performed by an in-network doctor), it may be expected that individuals will ask questions directed to the topic in a limited number of different ways; accordingly, the system may determine that fewer training questions are needed to train the classifier on a sufficient variety of questions. As a further example, a text classifier associated with a broad intent (e.g., prescription drug benefits) may need to be trained on a larger number of training questions due to the varied ways in which individuals phrase questions directed to the topic. The system may have assessed intent complexity based on previous iterations of generating training sets for the text classifier. For example, the system may have generated training sets with different numbers of questions. Based on the performance of the differently-sized training sets, the system may determine the appropriate training set size for subsequent training set construction.

At a block 230, the system selects questions for training the text classifier based on distances between the generated vectors of TF-IDF values. The distances characterize the degree of dissimilarity between the corresponding questions. That is, two questions that use mostly matching words or phrases will have a lower distance than two questions that use mostly different words or phrases. Furthermore, the extent of the distance may be based on the significance of the words or phrases found in one question but not the other. For example, if a word or phrase is infrequently used throughout the generated set of questions, but is used in a first question, then the absence of that word or phrase from a second question will contribute more to the distance between the first and second question than if the word or phrase was used frequently throughout the set of questions. To determine the distance between two vectors, the system may calculate the cosine distance $d_c$, where $$d_c = 1 - \frac{xy^T}{\|x\|\|y\|},$$

and x and y represent a first and second vector. The system may alternatively calculate the Euclidean distance $d_e$, where $d_e = 1 - \|x - y\|$, between the two vectors.

Figure 6:
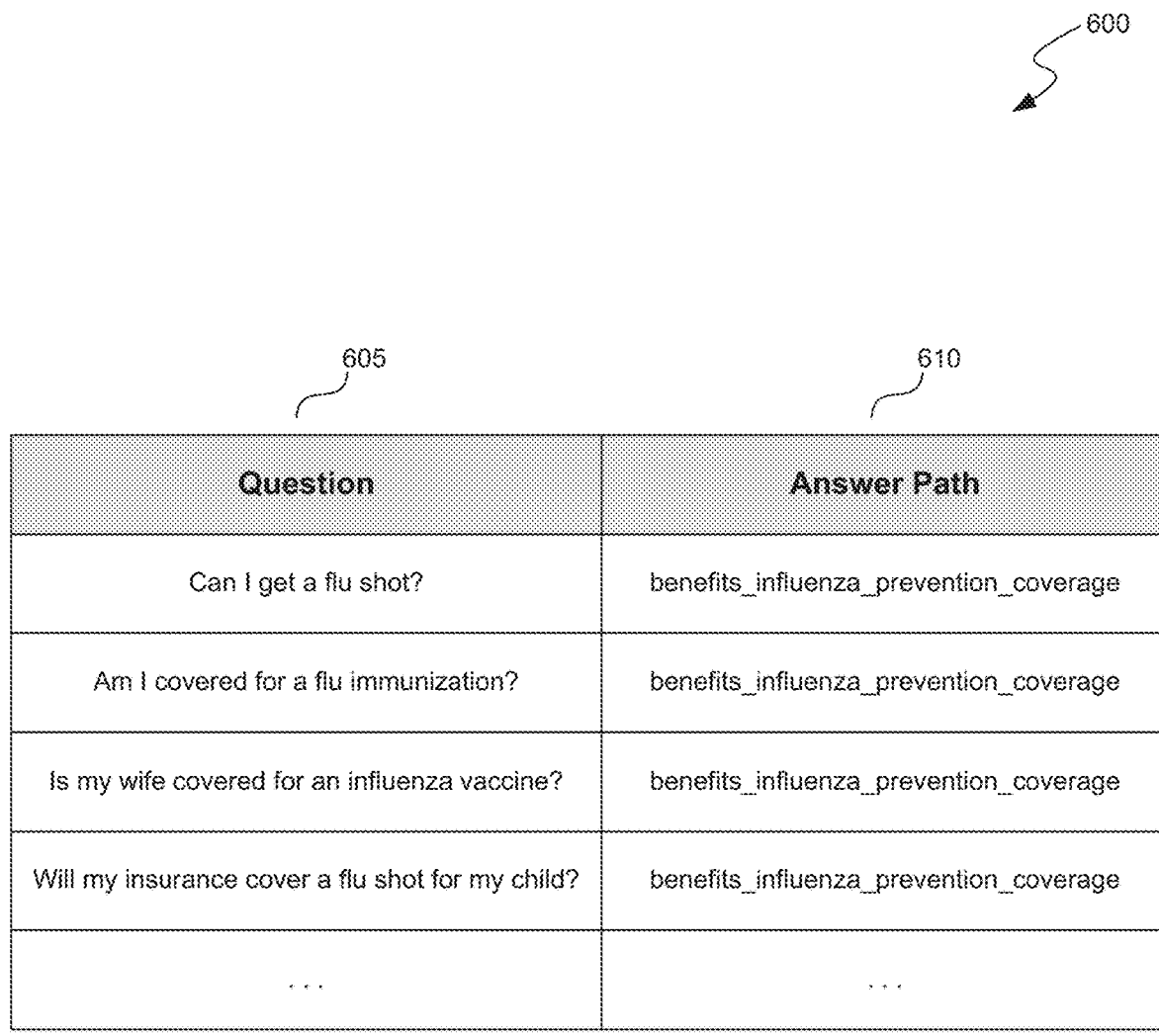
FIG. 6 is a reduced set of diverse questions for training a classifier.

To select questions for training, the system at block 230 performs pairwise distance calculations between the TF-IDF vectors of questions directed to the intent of the classifier. Based on the distance calculations, the system selects questions directed to the intent that achieves sufficient variety of question type. For example, the system may select questions based on a similarity reduction algorithm in which the system begins with a set of intent questions and then removes questions from the set that are too similar to other questions in the set (based on distance measures being too small) until the desired number of questions is reached. As a further example, the system may select questions based on a dissimilarity build-up algorithm in which the system the system begins with an empty set of questions, and then adds a generated intent question to the set, if the question is sufficiently dissimilar from the other questions in the set (based on a distance measure being large enough), until the set contains the desired number of questions is reached. Whether using similarity reduction or dissimilarity build-up, the system may adjust distance thresholds until the desired number of questions is reached (e.g., making it more likely for questions being from an initial set for being too similar, or making it more likely for questions to be added to a set for being sufficiently dissimilar). It will be appreciated that other evaluative techniques and algorithms may be used to construct a training set, with a sufficient number of questions and a sufficient variety of question types, based on evaluations of distances associated with different question combinations. FIG. 6 illustrates a training set 600 generated by the system. The training set, reduced from the example set of generated questions 400 in FIG. 4, are illustrative of an example set of questions 605 that provide sufficient variety to train a text classifier on questions related to the corresponding topic (as indicated by answer path 610).

Returning to FIG. 2, at a block 235 the system trains the appropriate text classifier using the selected set of training questions. The classifier may be trained, for example, using supervising machine learning training techniques. Once trained, the text classifier may be used as part of an automated inquiry service to determine whether natural language queries should be classified as being directed to the associated topic. For example, in the context of an automated inquiry service used to respond to questions from insured individuals regarding their health benefits, a first classifier may be used to determine whether the individual is asking about coverage for insulin injectors, a second classifier may be used to determine whether the individual is asking about coverage for flu shots, etc. Based on the determination of the question classification, the automated inquiry service responds to the individual with a relevant answer.

At a block 240, the system receives feedback that may be used to enhance the classifier. As a first example, the system may receive feedback regarding the accuracy of a provided response. For example, an individual may provide the system with explicit feedback that indicates whether or not the provided response addressed the individual's question. That is, the feedback may indicate that the response was relevant to the individual's question or may indicate that the response appears to the individual to be directed to a different question.

As a second example of feedback received at the block 240, the system may analyze questions received from individuals and compare the received questions against the training sets to identify new questions that exhibit large dissimilarity and could improve the training sets. For example, for a received question the system may identify the intent to which the question is directed and the training set used for that intent. The system may then assess the measure of dissimilarity between the question and the questions in the identified training set. Dissimilarity may be measured based on the vector distance between the received question and the training set questions. In some embodiments the system extracts phrase entities (e.g., intents, pronouns, locations, etc.) from the training set questions and received question to derive question forms. The distance between the question form of the received question and the question forms of the training set may be used to determine if the received question is sufficiently dissimilar. If the received question is sufficiently dissimilar it is added to the training set for the relevant intent, so that it may be used during subsequent retraining of the corresponding classifier.

At a block 245, the system retrains the classifier based on received feedback. By performing retraining based on real-world individual feedback, the system is able to improve its ability to accurately classify and respond to individual queries. The process then returns to block 240 to receive additional feedback for retraining.

Higher-Rank Question Representations

Although the ground truth expansion system has been described as utilizing vectors that characterize each question, it will be appreciated that the system can utilize higher-rank question characterizations. For example, instead of constructing an n-gram or skip-gram vector for a question (where each vector element is the TF-IDF value for an n-gram or skip-gram in the question), the system can construct a question tensor. Each dimension, or mode, of the question tensor corresponds to a different way of segmenting the question. For example, a first mode may correspond to word bigrams, a second mode may correspond to Parts of Speech skip-grams, etc. Columns can correspond to the respective TF-IDF values for each question. That is, the tensor characterization of a question may be made up of one collection of TF-IDF values according to one type of segmentation of the question, another collection of TF-IDF values according to another type of segmentation of the question, etc. Constructing each collection of TF-IDF values may be performed in a manner similar to the one described for constructing a question vector, such as was illustrated by the process 220 of FIG. 2. The tensor characterization of the question thus captures a larger set of measurements of the statistical significance of words or phrases making up the question. Each mode in the question tensor merely represents a different way of representing the corresponding sentence.

Figure 7:
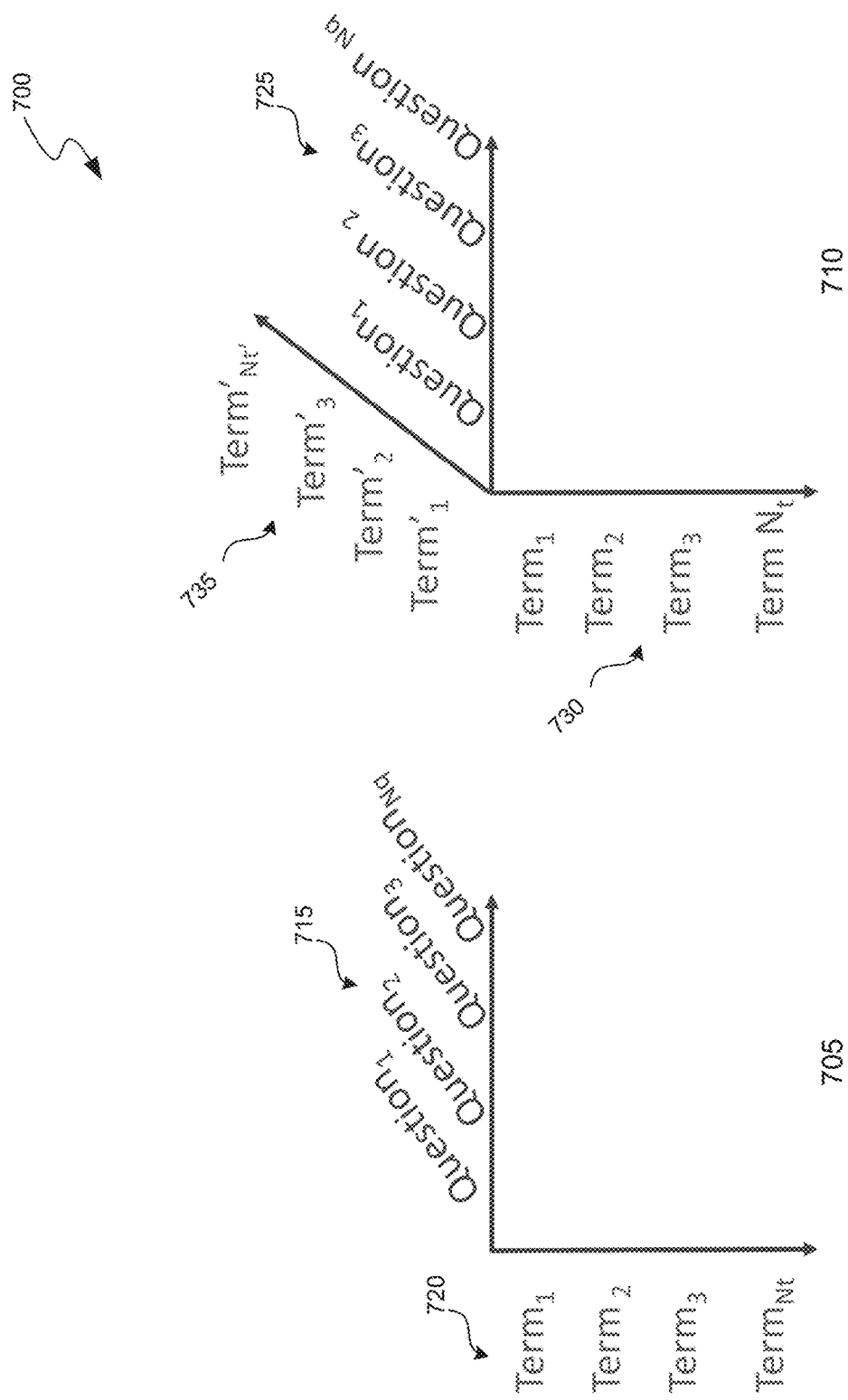
FIG. 7 is an illustration of different ways in which generated questions can be characterized.

FIG. 7 illustrates a vector characterization 705 and tensor characterization 710 of candidate questions generated by the system. The vector characterization 705 includes candidate questions 715 in one dimension and TF-IDF values for different terms 720 in another dimension. As described herein, the terms 720 can be any sized n-gram or skip-gram based on words, Parts of Speech, etc. However, all of terms 720 are constructed the same. That is, questions 715 are all segmented into the same form of n-gram or skip-gram.

Similarly, tensor characterization 710 also includes candidate questions 725 in a first dimension and TF-IDF values for different terms 730 in a second dimension. The tensor characterization 710 additionally includes TF-IDF values for a different construction of terms, or terms-prime 735, in a third dimension. Terms-prime 735 can be constructed differently than terms 730. That is, for example, if terms 730 are constructed out of unigrams of words, terms 735 may be constructed out of bigrams of syllables, skip-grams of Parts of Speech, etc. It will be appreciated that other combinations of forms for terms 730 and terms-prime 735 may be used, and that the tensor characterization 710 may include additional dimensions with additional term constructions.

Once question tensors have been constructed for candidate questions in an expanded set, the system uses the question tensors to identify dissimilar questions. For example, the system can calculate the distances between the different planes of the different question tensors. Using the planar distances, the system selects the set of dissimilar questions for a training set, such as was illustrated by block 230 of FIG. 2.

CONCLUSION

The above Detailed Description of examples of the disclosed technology is not intended to be exhaustive or to limit the disclosed technology to the precise form disclosed above. While specific examples for the disclosed technology are described above for illustrative purposes, various equivalent modifications are possible within the scope of the disclosed technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further, any specific numbers noted herein are only examples: alternative implementations may employ differing values or ranges.

These and other changes can be made to the disclosed technology in light of the above Detailed Description. While the above description describes certain examples of the disclosed technology, and describes the best mode contemplated, no matter how detailed the above appears in text, the disclosed technology can be practiced in many ways. Details of the system may vary considerably in its specific implementation, while still being encompassed by the technology disclosed herein. As noted above, particular terminology used when describing certain features or aspects of the disclosed technology should not be taken to imply that the terminology is being redefined herein to be restricted to any specific characteristics, features, or aspects of the disclosed technology with which that terminology is associated. In general, the terms used in the following claims should not be construed to limit the disclosed technology to the specific examples disclosed in the specification, unless the above Detailed Description section explicitly defines such terms.

We claim:

1. A computer-implemented method for generating a ground truth for training a text classifier, the method comprising:
   retrieving a plurality of question forms and a plurality of intent forms, wherein each intent form includes an intent identifier, at least one intent synonyms, and answer information;
   generating, based on the question forms and intent forms, an expanded question set comprised of question text and corresponding answers, wherein each question text-answer pair is associated with a topic;
   constructing vectors characterizing the questions of the expanded question set by, for each question text:
      dividing the question text into one or more text segments;
      calculating metrics of significance for the one or more text segments; and
      generating a vector associated with the question text comprised of the metrics of significance for the one or more text segments;
   determining a number of question text-answer pairs needed to train a text classifier based on a topic associated with the text classifier;
   generating a ground truth training set for training the text classifier by:
      identifying question text-answer pairs from the expanded question set associated with the topic of the text classifier;
      calculating vector distances between the vector characterizations of the identified question text-answer pairs; and
      selecting, based on the vector distances, question text-answer pairs for the ground truth training set based on the determined number needed to train the text classifier; and
   training the text classifier using the ground truth training set.

2. The method of claim 1, further comprising:
   receiving text classifier feedback; and
   retraining the text classifier based on the received feedback.

3. The method of claim 1, further comprising:
   receiving a question associated with the text classifier;
   determining a measure of dissimilarity between the received question and the ground truth training set;
   adding, based on the measure of dissimilarity, the received question to the ground truth training set; and
   retraining the text classifier based on the ground truth training set.

4. The method of claim 1, wherein the text segment metric of significance is a term frequency-inverse document frequency (TF-IDF) value, and wherein the TF-IDF value for a question text segment is based on the number of occurrences of the text segment in the question text and the number of question texts in the expanded question set in which the text segment occurs.

5. The method of claim 1, wherein the text segment is a unigram, bigram, or skip-gram.

6. The method of claim 1, wherein the vector distances are calculated based on the cosine distance between the two vectors.

7. The method of claim 1, wherein the selection of the question text-answer pairs for the ground truth training set comprises:
   determining a threshold dissimilarity vector distance;
   initializing an empty set of training questions; and
   for each of the identified question text-answer pairs, adding the identified question text-answer pair to the set of training questions when the vector distance between the identified question text-answer pair and a question text-answer pair of the training set exceeds the threshold dissimilarity vector distance.

8. The method of claim 1, wherein the selection of the question text-answer pairs for the ground truth training set comprises:
   determining a threshold similarity vector distance;
   constructing a set of training questions comprised of the identified question text-answer pairs; and
   for each question text-answer pair of the set of training questions, removing the question text-answer pair from the training set when the vector distance between the question text-answer pair and a second question text-answer pair of the training set exceeds the similarity threshold distance.

9. A non-transitory computer-readable medium containing instruction configured to cause one or more processors to perform a method of generating a ground truth for training a text classifier, the method comprising:
   retrieving a plurality of question forms and a plurality of intent forms, wherein each intent form includes an intent identifier, at least one intent synonyms, and answer information;
   generating, based on the question forms and intent forms, an expanded question set comprised of question text and corresponding answers, wherein each question text-answer pair is associated with a topic;
   constructing vectors characterizing the questions of the expanded question set by, for each question text:
      dividing the question text into one or more text segments;
      calculating metrics of significance for the one or more text segments; and
      generating a vector associated with the question text comprised of the metrics of significance for the one or more text segments;

determining a number of question text-answer pairs needed to train a text classifier based on a topic associated with the text classifier;

generating a ground truth training set for training the text classifier by:

identifying question text-answer pairs from the expanded question set associated with the topic of the text classifier;

calculating vector distances between the vector characterizations of the identified question text-answer pairs; and selecting, based on the vector distances, question text-answer pairs for the ground truth training set based on the determined number needed to train the text classifier; and training the text classifier using the ground truth training set.

10. The non-transitory computer-readable medium of claim 9, wherein the method further comprises:

receiving text classifier feedback; and retraining the text classifier based on the received feedback.

11. The non-transitory computer-readable medium of claim 9, wherein the method further comprises:

receiving a question associated with the text classifier;

determining a measure of dissimilarity between the received question and the ground truth training set;

adding, based on the measure of dissimilarity, the received question to the ground truth training set; and retraining the text classifier based on the ground truth training set.

12. The non-transitory computer-readable medium of claim 9, wherein the text segment metric of significance is a term frequency-inverse document frequency (TF-IDF) value, and wherein the TF-IDF value for a question text segment is based on the number of occurrences of the text segment in the question text and the number of question texts in the expanded question set in which the text segment occurs.

13. The non-transitory computer-readable medium of claim 9, wherein the text segment is a unigram, bigram, or skip-gram.

14. The non-transitory computer-readable medium of claim 9, wherein the vector distances are calculated based on the cosine distance between the two vectors.

15. The non-transitory computer-readable medium of claim 9, wherein the selection of the question text-answer pairs for the ground truth training set comprises:

determining a threshold dissimilarity vector distance;

initializing an empty set of training questions; and for each of the identified question text-answer pairs, adding the identified question text-answer pair to the set of training questions when the vector distance between the identified question text-answer pair and a question text-answer pair of the training set exceeds the threshold dissimilarity vector distance.

16. The non-transitory computer-readable medium of claim 9, wherein the selection of the question text-answer pairs for the ground truth training set comprises:

determining a threshold similarity vector distance;

constructing a set of training questions comprised of the identified question text-answer pairs; and for each question text-answer pair of the set of training questions, removing the question text-answer pair from the training set when the vector distance between the question text-answer pair and a second question text-answer pair of the training set exceeds the similarity threshold distance.

* * * * *